(12) United States Patent
Nam et al.

(10) Patent No.: US 9,189,592 B2
(45) Date of Patent: Nov. 17, 2015

(54) TESTER APPARATUS FOR OBTAINING FORMING LIMIT DIAGRAM

(71) Applicant: SAMSUNG ELECTRONICS CO., LTD., Suwon-si, Gyeonggi-do (KR)

(72) Inventors: Ki Ju Nam, Suwon-si (KR); Jun Beom Lee, Suwon-si (KR); Yong Kyun Cho, Suwon-si (KR)

(73) Assignee: SAMSUNG ELECTRONICS CO., LTD., Suwon-Si (KR)

( * ) Notice: Subject to any disclaimer, the term of this patent is extended or adjusted under 35 U.S.C. 154(b) by 375 days.

(21) Appl. No.: 13/709,869

(22) Filed: Dec. 10, 2012

(65) Prior Publication Data

US 2013/0152706 A1 Jun. 20, 2013

(30) Foreign Application Priority Data

Dec. 15, 2011 (KR) ........................ 10-2011-0135311

(51) Int. Cl.
| | | |
|---|---|---|
| *G06F 17/50* | (2006.01) | |
| *G01N 3/08* | (2006.01) | |
| *G01N 3/04* | (2006.01) | |
| *B21D 22/02* | (2006.01) | |

(52) U.S. Cl.
CPC .............. *G06F 17/5086* (2013.01); *G01N 3/04* (2013.01); *G01N 3/08* (2013.01); *B21D 22/02* (2013.01); *G06F 2217/41* (2013.01); *Y02T 10/82* (2013.01)

(58) Field of Classification Search
CPC . G06F 17/5086; G06F 2217/41; B21D 22/00; B21D 22/02; Y02T 10/82; G01N 3/04; G01N 3/08

USPC .................. 73/78–87, 760–860, 12.01–12.14
See application file for complete search history.

(56) References Cited

U.S. PATENT DOCUMENTS

| | | | | |
|---|---|---|---|---|
| 850,832 | A * | 4/1907 | Harris .............................. | 73/838 |
| 1,237,051 | A * | 8/1917 | Kammerer ....................... | 73/839 |
| 1,371,050 | A * | 3/1921 | Olsen ................................ | 73/87 |
| 2,262,084 | A * | 11/1941 | Alexander ......................... | 73/87 |
| 3,548,647 | A * | 12/1970 | Zacios ............................ | 73/839 |
| 3,618,372 | A * | 11/1971 | Beckstrom ....................... | 73/839 |
| 4,735,092 | A * | 4/1988 | Kenny ............................ | 73/840 |
| 5,507,189 | A * | 4/1996 | Kim et al. ....................... | 73/838 |
| 6,279,404 | B1 * | 8/2001 | Whelan et al. .................. | 73/800 |
| 6,860,156 | B1 * | 3/2005 | Cavallaro et al. .............. | 73/819 |
| 8,042,405 | B2 * | 10/2011 | Shuaib et al. ................... | 73/799 |
| 8,464,591 | B2 * | 6/2013 | Kuwayama et al. ............ | 73/799 |

(Continued)

FOREIGN PATENT DOCUMENTS

| | | | |
|---|---|---|---|
| CN | 201397274 | * | 2/2010 |
| CN | 102156080 | * | 8/2011 |

(Continued)

*Primary Examiner* — John Fitzgerald
(74) *Attorney, Agent, or Firm* — Staas & Halsey LLP (57) ABSTRACT

A tester apparatus capable of obtaining a forming limit diagram pertaining to a sample having a high degree of precision includes a fixing jig and a mobile jig installed at an upper side of the fixing jig so as to enable a vertical movement. The mobile jig may be configured to fix the sample in cooperation with the fixing jig, and a driving apparatus disposed at a lower side of the fixing jig may be configured to drive the vertical movement of the mobile jig. An interlocking apparatus provided in between the mobile jig and the driving apparatus may be configured to deliver a driving force of the driving apparatus to the mobile jig.

21 Claims, 5 Drawing Sheets

(56) References Cited

U.S. PATENT DOCUMENTS

8,479,589 B2 * 7/2013 Shuaib et al. .................. 73/799
2009/0235718 A1 * 9/2009 Fox .............................. 73/12.06

FOREIGN PATENT DOCUMENTS

| KR | 10-2002-0052868 | 7/2002 |
| KR | 10-2003-0059923 | 7/2003 |

* cited by examiner

TESTER APPARATUS FOR OBTAINING FORMING LIMIT DIAGRAM

CROSS-REFERENCE TO RELATED APPLICATIONS

This application claims the priority benefit of Korean Patent Application No. 10-2011-0135311, filed on Dec. 15, 2011, in the Korean Intellectual Property Office, the disclosure of which is incorporated herein by reference.

BACKGROUND

1. Field

Embodiments disclosed herein relate to a tester apparatus for obtaining a forming limit diagram from basic physical properties of a sample which is a forming material.

2. Description of the Related Art

Recently, when developing a product, CAM (Computer Aided Manufacturing) applications in mold design are increasingly used to reduce a production time of the product and to respond to the diversification of the product lineups.

CAM applications in mold design may be used during the production process of a product and enable the confirmation and the modification of a process result prior to the production of a product. Additionally, when changing the design of a product, CAM applications enable a product to be improved effectively and efficiently by saving time and reducing costs.

In order to obtain a superior result by use of CAM applications when designing a product, physical properties and characteristics of the forming material used in molding design need to be obtained beforehand. In general, basic tests which are used to obtain the properties of a pressed metallic panel include a tensile test, a FLD (Forming Limit Diagram) test, and a friction coefficient assessment test. Among the above-mentioned tests, the FLD test is considered as an important tool in determining the forming limit of a panel. However, if the FLD test is conducted in a general press facility without having an exclusive test apparatus configured to obtain the forming limit diagram, due to the characteristics of the press facility, a precise control of a stroke may be difficult, and thus the degree of precision of the test may be reduced.

Particularly, as the introduction of hot press forming is increasingly being used, the high-temperature forming limit diagram may be needed to be obtained, and thus a need exists for developing an exclusive test apparatus configured to obtain a hot forming limit diagram, in addition to a cold forming limit diagram, which may be used to derive the physical properties and characteristics of the forming material used in molding design, and used by CAM applications.

SUMMARY

Therefore, it is an aspect of the present disclosure to provide a tester apparatus for obtaining a forming limit diagram capable of obtaining the forming limit diagram having a high degree of precision.

It is another aspect of the present disclosure to provide a tester apparatus for obtaining a forming limit diagram capable of obtaining a hot forming limit diagram in addition to a cold forming limit diagram.

Additional aspects of the disclosure will be set forth in part in the description which follows and, in part, will be apparent from the description, or may be learned by practice of the disclosure.

In accordance with one aspect of the present disclosure, a tester apparatus includes a fixing jig, a mobile jig, a driving apparatus and an interlocking apparatus. The fixing jig allows a sample to be placed thereon. The mobile jig may be installed at an upper side of the fixing jig so as to enable a vertical movement and may be configured to fix the sample in cooperation with the fixing jig. The driving apparatus may be disposed at a lower side of the fixing jig and may be configured to drive the vertical movement of the mobile jig. The interlocking apparatus may be provided in between the mobile jig and the driving apparatus and configured to deliver a driving force of the driving apparatus to the mobile jig.

The interlocking apparatus may include a driving plate configured to be driven by the driving apparatus, and a plurality of connecting rods coupled in between the driving plate and the mobile jig and disposed in a parallel manner.

A penetrating hole may be provided at the fixing jig so that the connecting rod penetrates the fixing jig.

A heater may be installed at the fixing jig to heat the fixing jig.

A heater may be installed at the mobile jig to heat the mobile jig.

The tester apparatus may further include a punch installed at an upper side of the mobile jig in a movable manner in a vertical direction to perform a forming on the sample.

A guide rod may be formed at a lower surface of the punch and a guider may be provided at the mobile jig to guide forward and backward movements of the guide rod.

A processing hole may be provided at each of the mobile jig and the fixing jig so that the punch penetrates through the mobile jig and the fixing jig.

A fixing protrusion, which is configured to fix the sample, and a fixing groove, which corresponds to the fixing protrusion, may be provided at surroundings of the processing hole.

A measurement apparatus may be installed at an upper portion of the punch to measure a load applied to the sample by the punch.

A temperature controlling apparatus may be installed at the punch.

The tester apparatus may further include a camera unit disposed at a lower side of the fixing jig for an observation of the sample.

The driving apparatus may include a hydraulic cylinder or an electric motor.

In accordance with another aspect of the preset disclosure, a tester apparatus for obtaining a forming limit diagram includes a fixing jig, a mobile jig, and a heater. The mobile jig may be disposed at an upper side of the fixing jig and provided in a movable manner in a vertical direction with respect to the fixing jig. The heater may be installed in between the fixing jig and the mobile jig for the heating of the fixing jig and the mobile jig and/or the sample.

The heater installed in between the fixing jig and the mobile jig may include a high frequency heating coil. A plurality of heaters may also be internally disposed horizontally in at least one of the fixing jig and the mobile jig. A radiation panel may further be disposed at a lower surface of the fixing jig to prevent heat transfer to a lower side of the fixing jig.

In accordance with another aspect of the present disclosure, a method for performing a forming limit diagram test on a sample using a tester apparatus may include: selectively activating a heating element disposed between a fixing jig configured to accommodate the sample on an upper surface thereof and a mobile jig disposed adjacent to the upper surface of the fixing jig, according to whether a hot rolling or a cold rolling is performed; selectively activating at least one heater disposed internally in at least one of the fixing jig and the mobile jig, according to whether a hot rolling or a cold rolling is performed; lowering the mobile jig to fix the sample between the mobile jig and the fixing jig by operating a driving apparatus to drive a vertical movement of the mobile jig; lowering a punch installed at an upper side of the mobile jig to perform a forming on the sample; and terminating the lowering of the punch when the sample fractures.

The method for performing a forming limit diagram test on a sample may further include controlling a temperature of the punch to maintain a temperature of the punch between about −20° C. to about 20° C.

If a hot rolling is performed, the heating element may be activated to heat the sample to a predetermined temperature. For example, the sample may be heated to at or above about 900° C. If a hot rolling is performed the at least one heater may be activated to preheat at least one of the mobile jig and the fixing jig to a predetermined temperature, before the lowering of the mobile jig. For example, the at least one of the mobile jig and the fixing jig may be preheated to about 200° C.

BRIEF DESCRIPTION OF THE DRAWINGS

These and/or other aspects of the disclosure will become apparent and more readily appreciated from the following description of the embodiments, taken in conjunction with the accompanying drawings of which.

DETAILED DESCRIPTION

Reference will now be made in detail to the embodiments of the present disclosure, examples of which are illustrated in the accompanying drawings, wherein like reference numerals refer to like elements throughout.

Figure 1:
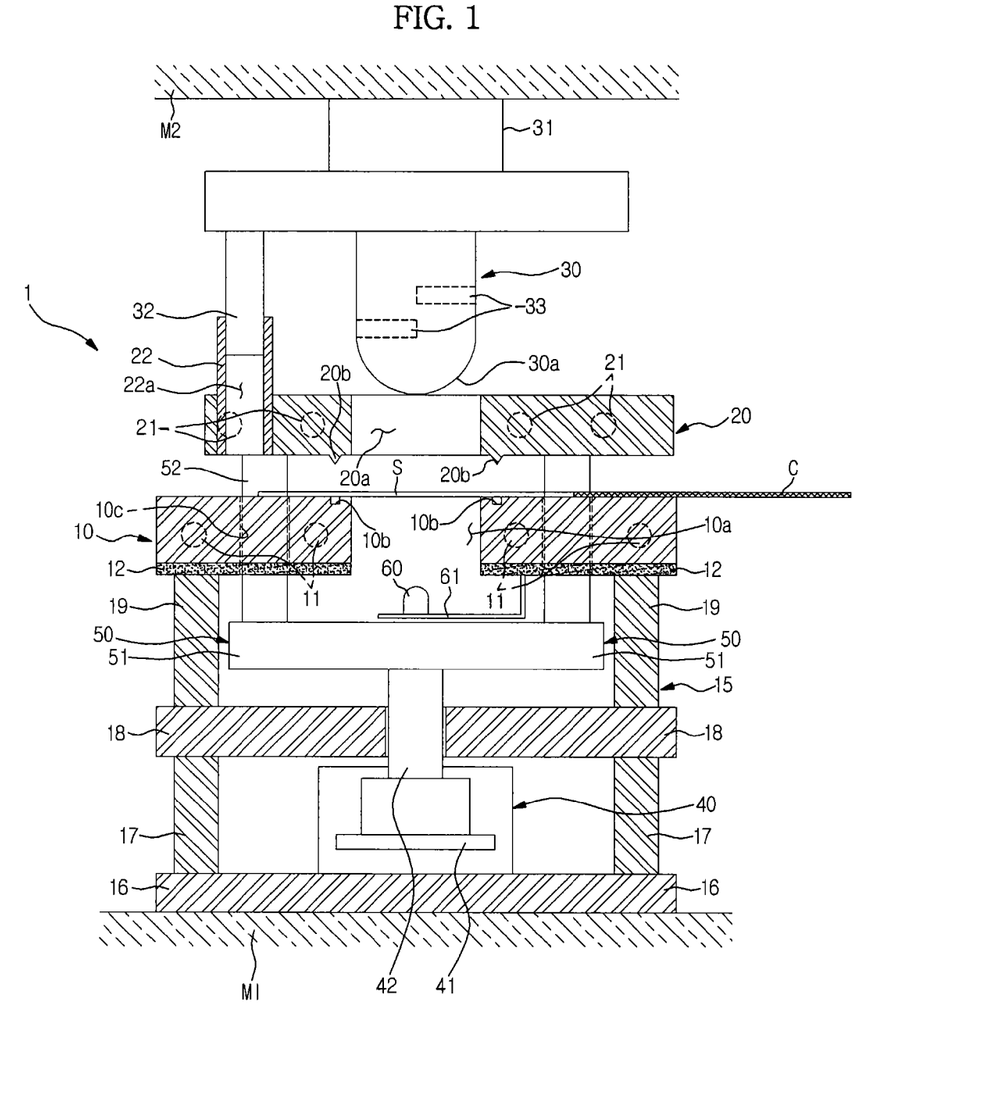
FIG. 1 is a cross-sectional view of a tester apparatus for obtaining a forming limit diagram in accordance with one embodiment of the present disclosure.

As illustrated in FIG. 1, a tester apparatus used to obtain a forming limit diagram 1 includes a fixing jig 10 and a mobile jig 20 that are configured to fix a sample 'S', a punch 30 configured to apply pressure and perform a forming on the sample 'S', a driving apparatus 40 configured to drive the mobile jig 20 to be moved in a vertical direction, and an interlocking apparatus 50 configured to connect in between the mobile jig 20 and the driving apparatus 40. The sample 'S' may be sheet metal or a other metallic panel, for example. However, sample 'S' may comprise other materials which may be tested and need not be limited to sheet metal or metallic panels.

The fixing jig 10 is formed in a plate type, and a processing hole 10a may be formed at a central portion of the fixing jig 10 to form a space through which the sample 'S' and the punch 30 pass when the punch 30 performs a forming on the sample 'S'. A heater 11 may be disposed at an inside of the fixing jig 10 so that when a test to obtain a hot forming limit diagram is to be conducted, the fixing jig 10 may be pre-heated before a forming is performed. The heater 11 may be formed with a cartridge heater having a shape of a bar, and may be installed in an inserted manner into an installation hole that is formed at the fixing jig 10 in a horizontal direction. There may be a plurality of installation holes formed in the fixing jig 10 to accommodate one or more heaters.

At a lower side of the fixing jig 10, a main frame 15 is provided to support the fixing jig 10. The main frame 15 may include a first base 16, a second base 18, a first supporting member 17, and a second supporting member 19. The second base 18 may be disposed such that it is spaced apart from the first base 16 in a vertical direction. The first supporting member 17 may support the first base 16 and the second base 18 by dispersing the weight applied in between the first base 16 and the second base 18 while being disposed in a parallel manner in between the first base 16 and the second base 18. The second supporting member 19 may support the second base 18 and the fixing jig 10 by dispersing the weight applied in between the second base 18 and the fixing jig 10 while being disposed in a parallel manner in between the second base 18 and the fixing jig 10.

At a lower surface of the fixing jig 10, a heat radiation panel 12 may be installed to prevent heat, which is generated by the heater 11 internally installed at the fixing jig 10, from being transferred to a lower side of the fixing jig 10. While FIG. 1 illustrates a heat radiation panel being disposed on a lower portion of the fixing jig 10 the disclosure is not so limited. For example, heat radiation panels may be disposed in other locations of the testing apparatus to prevent heat transfer from the heaters disposed in the fixing jig and mobile jig. For example, a heat radiation panel may be disposed on an interior side of the mobile jig 20 adjacent to processing hole 20a and/or an upper side of the mobile jig 20, to prevent heat transfer to the punch 30 or to the guide rod 32, if desired.

The mobile jig 20 may be disposed at an upper side of the fixing jig 10, and may be provided in a movable manner in a vertical direction with respect to the fixing jig 10, so that the fixing and the separating of the sample 'S' may be possible before and after a forming limit diagram test is conducted with respect to the sample 'S'.

At the central portion of the mobile jig 20, similar to the case of the fixing jig 10, a processing hole 20a may be formed to form a space through which the sample 'S' and the punch 30 pass when the punch performs a forming on the sample 'S'. A heater 21 may be internally installed at the mobile jig 20 so that the mobile jig 20 is pre-heated at a predetermined temperature prior to a forming limit diagram test being conducted. The heater 21 may be composed of a cartridge heater, for example. The heater 21 may be installed in an inserted manner into an installation hole that is formed at the mobile jig 20 in a horizontal direction. There may be a plurality of installation holes formed in the mobile jig 20 to accommodate one or more heaters.

A fixing protrusion 20b configured to fix the sample 'S' may be provided at a surrounding portion of the processing hole 20a of the mobile jig 20. That is, the fixing protrusion 20b may be disposed at a lower surface of the mobile jig 20 adjacent to the processing hole 20a which is formed in the central portion of the mobile jig 20. A fixing groove 10b may be provided at a surrounding portion of the processing hole 10a of the fixing jig 10 such that the fixing groove 10b is configured to accommodate the fixing protrusion 20b and a portion of the sample 'S' deformed by the fixing protrusion 20b. That is, the fixing groove 10b may be disposed at an upper surface of the fixing jig 10 adjacent to the processing hole 10a which is formed in the central portion of the fixing jig 10.

In accordance with the embodiment illustrated, the fixing protrusion 20b may be provided at the mobile jig 20, and the fixing groove 10b may be provided at the fixing jig 10. However, the positions of the fixing protrusion 20b and the fixing groove 10b may be reversed, so that the protrusion may be provided at the fixing jig 10 while the fixing groove may be provided at the mobile jig 20.

For the forward and backward movements of the mobile jig 20, at a lower side of the mobile jig 20, the driving apparatus 40 may be configured to supply the driving force to drive the mobile jig 20, and the interlocking apparatus 50 may be configured to connect in between the mobile jig 20 and the driving apparatus 40.

The interlocking apparatus 50 may include a driving plate 51 configured to be driven by the driving apparatus 40, and a plurality of connecting rods 52 may be connected in between the driving plate 51 and the mobile jig 20.

One end of the connecting rod 52 may be coupled to a lower portion of the mobile jig 20, while the other end of the connecting rod 52 may be coupled to an upper portion of the driving plate 51. At the fixing jig 10, a penetrating hole 10c is provided so that the connecting rod 52 may be penetrated therethrough, and by the penetrating hole 10c, the linear movement in the vertical direction of the connecting rod 52 is guided. The connecting rod 52 may be composed in plurality, and may be disposed in parallel in between the mobile jig 20 and the driving plate 51.

The driving apparatus 40 may include a hydraulic apparatus (not shown) and a hydraulic cylinder 41 configured to operate by being connected to the hydraulic apparatus (not shown). The hydraulic cylinder 41 may be installed on the first base 16 of the main frame 15. A piston rod 42 of the hydraulic cylinder 41 may penetrate through the second base 18, and may be coupled to a lower portion of the driving plate 51. Thus, when the piston rod 42 is moved forward and backward in a vertical direction as the piston rod 42 of the hydraulic cylinder 41 is interlocked with the mobile jig 20, the mobile jig 20 is correspondingly moved forward and backward in a vertical direction by the interlocking apparatus 50.

A punch 30 may be disposed at an upper side of the mobile jig 20. The punch 30 may be configured to pressurize the sample 'S' to perform a forming on the sample 'S'.

Meanwhile, the tester apparatus for obtaining a forming limit diagram 1 in accordance with the present disclosure may be used to control a stroke of the punch 30, and may be applied for use as a commercialized test apparatus for a general use, such as a MTS (Material Test System).

Thus, a fixed unit M1 of the MTS may be disposed at a lower portion of the first base 16 to support the first base 16, and a mobile unit M2 of the MTS may be disposed at an upper portion of the punch 30 to move the punch 30 in a vertical direction. In between the mobile unit M2 and the punch 30, a rod cell 31 may be installed. For example, while the forming of the sample 'S' is performed using the punch 30, the weight that is applied on the punch by the mobile unit M2 of the MTS may be able to be monitored by the rod cell 31.

At one side of the punch 30, a guide rod 32 may be provided to guide the movement in a vertical direction of the punch 30, and at the mobile jig 20, a guider 22 to guide the forward and backward movement of the guide rod 32 may be provided. While FIG. 1 illustrates the guide rod 32 being disposed at one side of the punch 30 the disclosure is not so limited. For example, the guide rod 32 may be disposed at the other side of the punch 30 as well. Alternatively, a guide rod 32 may be provided on both sides of the punch 30 if desired.

The guide rod 32 may be formed in a shape of a cylinder, and at the guider 22, a guide hole 22a may be provided to accommodate the guide rod 32 while the guide rod 32 is moved forward and backward.

At a lower portion of the punch 30, a forming unit 30a having a semicircular shape may be formed so that the sample 'S' may be formed in a semicircular shape by the punch 30, and a temperature controlling apparatus 33 may be installed for the temperature control of the punch 30. The forming unit 30a may have shapes other than the semicircular shape if desired, for example, a triangular or rectangular shape.

At a lower portion of the fixing jig 10, a camera unit 60 may be disposed to monitor the deforming status of the sample 'S' when performing a forming on the sample 'S' to obtain a forming limit diagram.

The camera unit 60 may be disposed at a central portion of a lower portion of the processing hole 10a of the fixing jig 10 through the installation bracket 61, which is fixed to the fixing jig 10, so that the point in time when the break of the sample 'S' occurs may be monitored. Additionally, the camera unit 60 may record image data by taking a plurality of images which may be used to obtain the forming limit diagram. The camera unit 60 may include one or a plurality of cameras to monitor the deforming status of the sample 'S'. While FIG. 1 illustrates the camera unit being disposed at a central portion of a lower portion of the processing hole 10a via an installation bracket 61 fixed to a lower surface of one side of the fixing jig 10 the disclosure is not so limited. For example, the installation bracket 61 may be fixed to a lower surface of the other side of the fixing jig 10 as well. Alternatively, the installation bracket 61 may be fixed to a lower surfaces of both sides of the fixing jig 10 if desired.

Hereinafter, referring to FIGS. 1 to 4, a process of obtaining a forming limit diagram through a tester apparatus for obtaining a forming limit diagram in accordance with one embodiment of the present disclosure will be described.

First, for the test, the sample 'S' is prepared. At the sample 'S', a grid is formed so that the deformation rate of each portion of the sample 'S', which becomes the basic data for obtaining a forming limit diagram after the forming is performed by the punch 30, may be calculated. That is, a predetermined pattern or lines which make up the grid may be applied to the sample 'S' prior to the forming process. For example, the grid may be composed of a circular shape or a latticed shape. The grid may be selected in order to obtain accurate basic data after the forming is performed by the punch 30. In a case when obtaining a forming limit diagram at the time of a cold rolling is performed, the grid formed at the sample 'S' may be formed in a printed manner through a printed medium such as silkscreen. However, in a case when a hot rolling is performed, heat is needed to be applied with respect to the sample in the obtaining stage of the forming limit diagram, but a grid printed on the sample may be dissipated in a combusted manner in the heating stage of the sample. Thus, in a case of a hot rolling, a grid may be composed by forming patterns or lines (e.g., a circular shape of a latticed shape) on the sample 'S' by etching so as to avoid the grid being dissipated due to the heat being applied.

Once the sample 'S' is formed with a grid it may be placed at the fixing jig 10 as illustrated in FIG. 1. In a case of obtaining a forming limit diagram while a hot rolling is being performed, the sample 'S' may be configured to go through a process of being heated at or above about 900° C. through a high frequency heating coil 'C'. At this time, in order for enhancing the degree of precision of the test by having the temperature gradient in between the sample 'S' and the two jigs 10 and 20 minimized, the mobile jig 20 and the fixing jig 10 may be pre-heated to about 200° C. through the heaters 11 and 21. In addition, the temperature of the punch 30 may be controlled through the temperature controlling apparatus 33 so that the temperature of the punch 30 may be maintained from about −20° C. to about a room temperature (e.g., about 20° C.).

Figure 2:
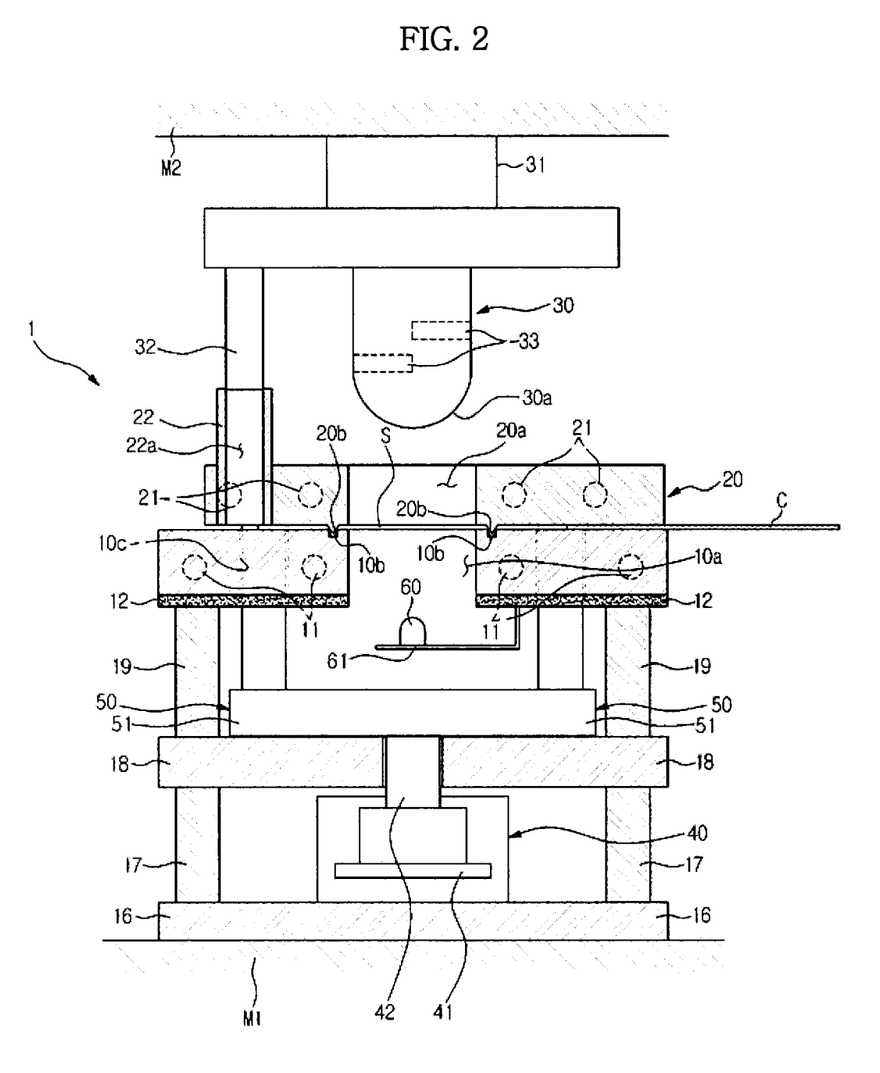
FIG. 2 is a drawing showing a status of a fixed sample.

When the heating process with respect to the sample is completed, as illustrated in FIG. 2, the driving apparatus 40 may be operated, and the mobile jig 20 is descended until the sample 'S' is completely fixed in between the fixing jig 10 and the mobile jig 20. That is, as can be seen from FIG. 2, the driving plate 51 is lowered, and correspondingly, the mobile jig 20 is lowered. The driving plate 51 may be lowered until the lower surface of the driving plate 51 is in contact with the upper surface of the second base 18. For example, the tester apparatus may be structured such that the distance the driving plate 51 is lowered until the lower surface of the driving plate 51 contacts the upper surface of the second base 18 may be equivalent to the distance that the mobile jig 20 is lowered until the fixing protrusion 20b disposed at the lower surface of the mobile jig 20 is fixed in the fixing groove 10b disposed at the upper surface of the fixing jig 10. Further, the camera unit 60 does not move and remains stationary, since it is fixed to the lower portion of the fixing jig 10 via the installation bracket 61.

Figure 3:
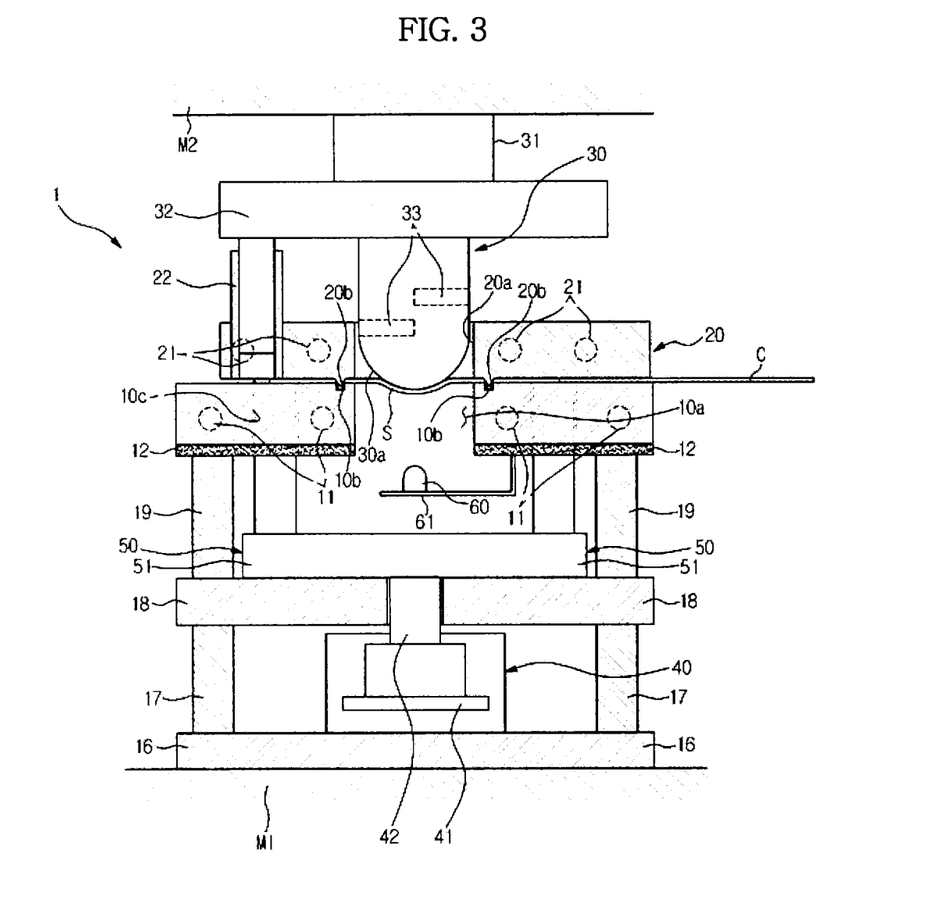
FIG. 3 is a drawing showing a status of a sample during the beginning of the forming process.

After fixing the sample 'S' between the fixing jig 10 and the mobile jig 20, as illustrated in FIG. 3, the MTS is operated to descend the punch 30, and the forming with respect to the sample 'S' is started. As can be seen from FIG. 3, as the punch 30 is lowered, the guide rod 32 may be lowered into the guider 22. The guide rod 32 may descend up to a distance equivalent to the length of the guide hole 22a, however the tester apparatus may be configured such that the punch 30 will come into contact with the sample 'S' before such a distance is traveled by the punch 30. As can be seen from FIG. 3, once the punch 30 comes into contact with the sample 'S', the sample 'S' becomes deformed. Camera unit 60 may capture images of the deforming of the sample 'S' while the punch 30 exerts a force on the sample's'. Rod cell 31 may assist in the control of the force exerted by the punch 30 by monitoring the weight that is applied on the punch 30 by the mobile unit M2.

Figure 4:
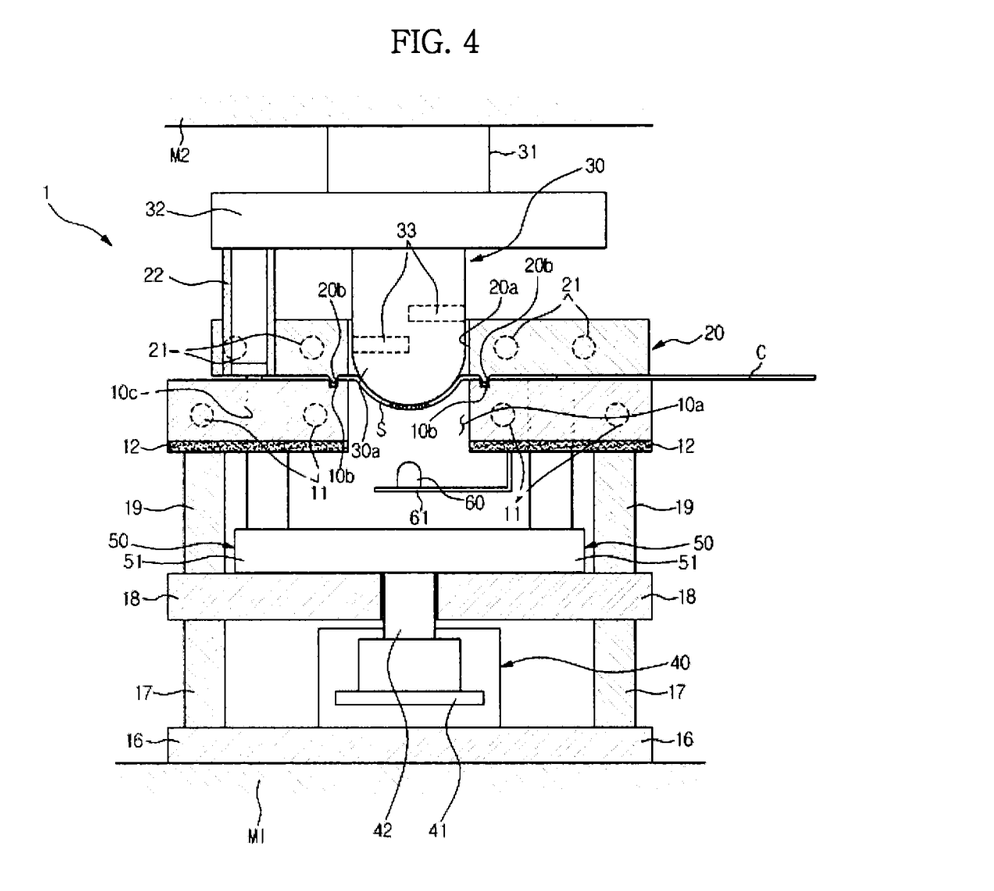
FIG. 4 is a drawing showing a status of a sample at an ending of the forming process when a break of the sample occurs.

As illustrated in FIG. 4, the punch 30 may be descended until the point in time when a break occurs at the sample 'S'. The point of time when a break occurs at the sample 'S' may be monitored through the camera unit 60, and when an occurrence of the break of the sample 'S' is found, the pressurization movement by the MTS is stopped immediately.

Next, the mobile unit M2 of the MTS and the punch 30 are moved backward by following the movements of the above in a reverse order. That is, the mobile jig 20 may be ascended so that the sample 'S' may be retrieved and analyzed. By interpreting the deformation of the grid formed on the sample 'S' after the sample 'S' is separated from the jigs 10 and 20, the data with respect to the major deformation rate and the minor deformation rate may be calculated, and on the basis of the obtained deformation rate data, the obtaining with respect to the forming limit diagram may finally be achieved. For example, properties regarding a strain limit that sample 'S' may endure may be measured based on an analysis of the deformation of the grid to obtain the forming limit diagram.

In a case of a cold rolling, the obtaining process of a forming limit diagram may be similarly performed while the heating process with respect to the sample and the jig are omitted from the process above.

Figure 5:
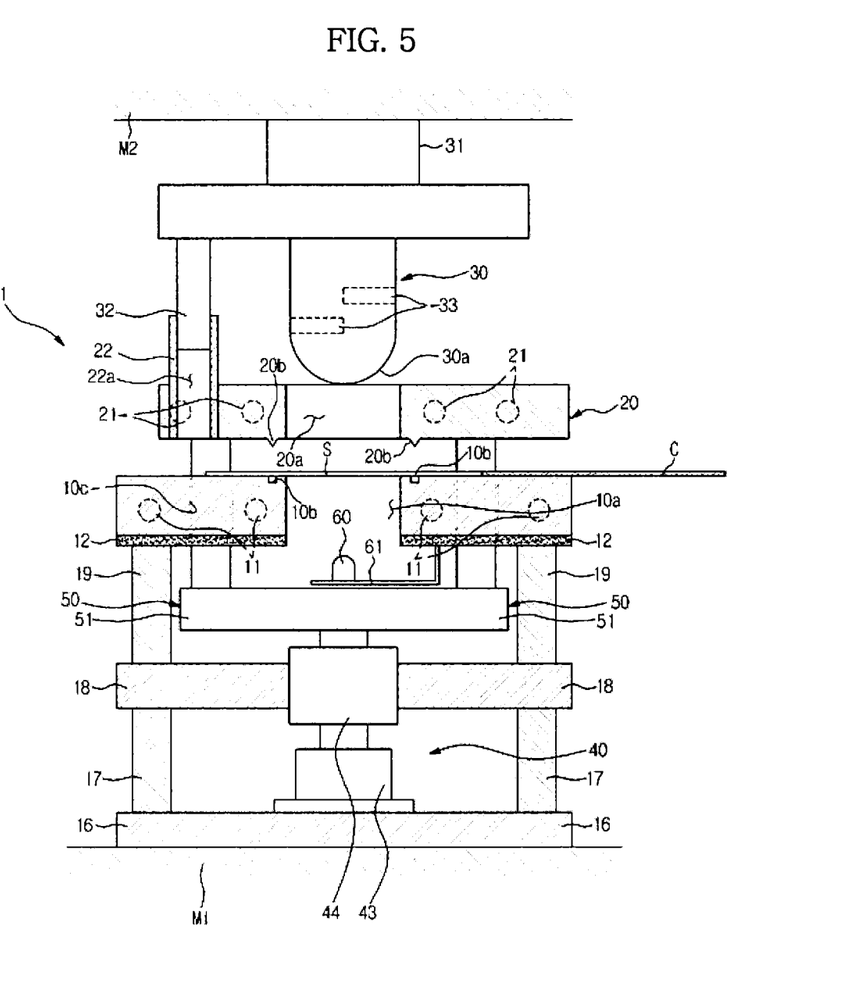
FIG. 5 is a cross-sectional view of a tester apparatus for obtaining a forming limit diagram in accordance with another embodiment of the present disclosure.

As shown in FIG. 5, a tester apparatus in accordance with another embodiment of the present disclosure is shown.

The difference of the present embodiment from the earlier embodiment is that an electric motor 43 may be used in place of the hydraulic cylinder 41 of the driving apparatus 40.

That is, from the earlier embodiment, the hydraulic cylinder 41 may be replaced with the electric motor 43. The electric motor 43 may be composed of a servo motor that is capable of controlling the number of rotations of the electric motor 43 and may be capable of rotating backward and forward.

In addition, to decelerate the rotation movement generated at the electric motor 43 and to boost the generated force, a booster apparatus 44 may be installed in between the electric motor 43 and the driving plate 51. Here, the booster apparatus 44 may be composed of a decelerating apparatus using a planetary gear.

According to the above described embodiments, a tester apparatus for obtaining a forming limit diagram for a sample and a method of operating the tester apparatus for obtaining a forming limit diagram of the sample has been disclosed which is capable of selectively performing a hot rolling and cold rolling test. The test apparatus in accordance with the above-described embodiments may include heaters disposed internally within the fixing jig and mobile jig. During a hot rolling, the fixing jig and mobile jig may be preheated to a predetermined temperature before the mobile jig is lowered to fix the sample between the mobile jig and fixing jig. The preheating of the mobile jig and fixing jig minimizes a difference in temperature between the sample which may be heated up to or above about 900° C. and the mobile jig and fixing jig. The tester apparatus includes a punch disposed at an upper side of the mobile jig which is lowered to perform a forming on the sample. The punch may include a guide rod disposed on one side of the punch which extends from a lower surface of the punch. The guide rod may be fitted within a guider which is disposed on an upper surface of the mobile jig, to guide movement of the punch when the punch is lowered. While the example embodiments disclosed herein have illustrated a testing apparatus having a punch and mobile jig which are moveable in a vertical direction, one of ordinary skill in the art would understand that, if desired, the testing apparatus may be modified or altered such that the configuration of the testing apparatus is capable of moving the punch and the mobile jig in a horizontal direction, or at an angle, to perform a forming on the sample.

Although a few example embodiments of the present disclosure have been shown and described, it would be appreciated by those skilled in the art that changes may be made to these embodiments without departing from the principles and spirit of the disclosure, the scope of which is defined in the claims and their equivalents.

What is claimed is:

1. A tester apparatus for obtaining a forming limit diagram, the tester apparatus comprising:
   a fixing jig configured to accommodate a sample on an upper surface of the fixing jig;
   a mobile jig installed adjacent to an upper side of the fixing jig which is configured to move in a vertical direction and configured to fix the sample in cooperation with the fixing jig, when a sample is placed on the fixing jig;
   a driving apparatus disposed at a lower side of the fixing jig configured to drive the vertical movement of the mobile jig;
   an interlocking apparatus provided in between the mobile jig and the driving apparatus configured to deliver a driving force of the driving apparatus to the mobile jig;
   a punch installed at an upper side of the mobile jig which is configured to move in a vertical direction to perform a forming on the sample;
   a guide rod which extends downward from a lower surface of the punch; and a guider provided at the mobile jig to guide forward and backward vertical movements of the guide rod.

2. The tester apparatus of claim 1, wherein:
a heater is installed at the fixing jig to heat the fixing jig.

3. The tester apparatus of claim 1, wherein:
a heater is installed at the mobile jig to heat the mobile jig.

4. The tester apparatus of claim 1, wherein:
a measurement apparatus is installed at an upper portion of the punch to measure a load applied to the sample by the punch.

5. The tester apparatus of claim 1, wherein:
a temperature controlling apparatus is installed at the punch.

6. The tester apparatus of claim 1, further comprising:
a camera unit disposed at a lower side of the fixing jig to observe the sample.

7. The tester apparatus of claim 1, wherein:
the driving apparatus comprises at least one of a hydraulic cylinder or an electric motor.

8. The tester apparatus of claim 1, wherein:
the interlocking apparatus comprises a driving plate configured to be driven by the driving apparatus, and a plurality of connecting rods coupled in between the driving plate and the mobile jig, disposed in a parallel manner.

9. The tester apparatus of claim 8, wherein the fixing jig includes a plurality of penetrating holes through which the plurality of connecting rods respectively penetrate to connect to the mobile jig.

10. The tester apparatus of claim 1, wherein the mobile jig and fixing jig each include a processing hole to provide a space for the punch to penetrate through the mobile jig and the fixing jig.

11. The tester apparatus of claim 10, wherein:
a fixing protrusion, which is configured to fix the sample, and a fixing groove, which corresponds to the fixing protrusion, are disposed adjacent to the processing hole.

12. A tester apparatus for obtaining a forming limit diagram, the tester apparatus comprising:
a fixing jig;
a mobile jig disposed at an upper side of the fixing jig and configured to move in a vertical direction with respect to the fixing jig;
a punch installed at an upper side of the mobile jig which is configured to move in a vertical direction;
a guide rod which extends downward from a lower surface of the punch;
a guider provided at the mobile jig to guide forward and backward vertical movements of the guide rod; and
a heater installed in between the fixing jig and the mobile jig to heat the fixing jig and the mobile jig.

13. The tester apparatus of claim 12, wherein the heater installed in between the fixing jig and the mobile jig includes a high frequency heating coil.

14. The tester apparatus of claim 12, wherein a plurality of heaters are internally disposed horizontally in at least one of the fixing jig and the mobile jig.

15. The tester apparatus of claim 13, further comprising a radiation panel disposed at a lower surface of the fixing jig to prevent heat transfer to a lower side of the fixing jig.

16. A method of performing a forming limit diagram test on a sample using a tester apparatus the method comprising:
selectively activating a heating element according to whether a hot rolling or a cold rolling is performed, the heating element being disposed between a fixing jig configured to accommodate the sample on an upper surface of the fixing jig, and a vertically adjustable mobile jig disposed adjacent to the upper surface of the fixing jig;
selectively activating at least one heater disposed internally in at least one of the fixing jig and the mobile jig, according to whether a hot rolling or a cold rolling is performed;
lowering the mobile jig to fix the sample between the mobile jig and the fixing jig, by operating a driving apparatus to drive a vertical movement of the mobile jig;
lowering a punch installed at an upper side of the mobile jig to perform a forming on the sample; and
terminating the lowering of the punch when the sample fractures.

17. The method of claim 16, further comprising controlling a temperature of the punch to maintain a temperature of the punch between about −20° C. to about 20° C.

18. The method of claim 16, wherein if a hot rolling is performed, the at least one heater is activated to preheat at least one of the mobile jig and the fixing jig to a predetermined temperature, before the lowering of the mobile jig.

19. The method of claim 18, wherein the at least one of the mobile jig and the fixing jig is preheated to about 200° C. before the lowering of the mobile jig.

20. The method of claim 16, wherein if a hot rolling is performed, the sample is heated to a predetermined temperature before the lowering of the mobile jig.

21. The method of claim 20, wherein the sample is heated to a predetermined temperature at or above about 900° C. before the lowering of the mobile jig.

* * * * *